(12) United States Patent
De Ioannes et al.

(10) Patent No.: US 6,916,908 B2
(45) Date of Patent: Jul. 12, 2005

(54) **PRODUCT AND COMPOSITION CONTAINING A *CONCHOLEPAS CONCHOLEPAS* HEMOCYANIN (CCH) SUBUNIT, AND A METHOD OF USE THEREOF**

(76) Inventors: Alfredo Emilio De Ioannes, Eduardo Castillo Velasco 2876, Santiago (CL); Maria Inés Becker, Eduardo Castillo Velasco 2876, Santiago (CL)

( * ) Notice: Subject to any disclaimer, the term of this patent is extended or adjusted under 35 U.S.C. 154(b) by 0 days.

(21) Appl. No.: 10/624,006

(22) Filed: Jul. 21, 2003

(65) Prior Publication Data

US 2005/0020486 A1 Jan. 27, 2005

(51) Int. Cl.$^7$ .......................... C07K 14/00; C07K 1/00; A61K 38/00
(52) U.S. Cl. .......................... 530/350; 530/857; 514/12
(58) Field of Search .......................... 514/12; 530/350; 424/175.1

(56) References Cited

FOREIGN PATENT DOCUMENTS

CL         2181-98        5/1999

OTHER PUBLICATIONS

Becker et al., Physico and Immunochemical Study of a New Immunogenic Protein of the Hemocyanin Family From the Mollusk *Concholepas concholepas* (CCH), Jul. 2001, 11th International Congress of Immunolgy, Stockholm Sweden, Abstract, A5.Mon.5.1/1277.*

Linn et al., Keyhole Limpet Heamocyanin in Experimental Bladder Cancer, 2000, European Urology, 37(Suppl. 3), 34–40.*

Calbiochem catalog, 2000–2001, p. 730, available for public purchase, *Concholepas concholepas* hemocyanin.*

R. D. Swerdlow et al., "Immunotherapy with Keyhole Limpet Hemocyanin: Efficacy and Safety in the MB–49 Intravesical Murine Bladder Tumor Model", The Journal of Urology, Jun. 1994, 1718–1722, vol. 151, American Urological Associations, Inc.

W. Gebauer et al, "Quaternary structure, subunits and domain patterns of two discrete forms of keyhole limpet hemocyanin: KLH1 and KLH2", Zoology 96 (1994), pp. 51–68, Institute of Zoology, Univ. of Mainz, Germany.

H. Oliva et al., "Monclonal Antibodies to Mulluskan Hemocyanin from *Concholepas concholepas* Demonstrate Common and Specific Epitopes among Subunits," Hybridoma and Hybridomics, vol. 21, No. 5, 2002, Mary Ann Liebert, Inc.

* cited by examiner

*Primary Examiner*—Jon Weber
*Assistant Examiner*—Suzanne M. Mayer
(74) *Attorney, Agent, or Firm*—Daniel F. Nesbitt; Hasse & Nesbitt LLC

(57) ABSTRACT

The use of CCH-A subunit isolated from hemocyanin of the marine gastropod *Concholepas concholepas* (CCH), or a combination thereof, as an immunostimulant agent in the innate or adaptive immune response of vertebrates or as an immunotherapeutic agent in cancer of either humans or animals, where the CCH-A subunit has a molecular weight of about 404 kDa, is stable in the absence of $Ca^{+2}$ and $Mg^{+2}$ and is at least 95% pure.

15 Claims, 4 Drawing Sheets

PRODUCT AND COMPOSITION CONTAINING A *CONCHOLEPAS CONCHOLEPAS* HEMOCYANIN (CCH) SUBUNIT, AND A METHOD OF USE THEREOF

FIELD OF THE INVENTION

The present invention refers broadly to the use of a novel hemocyanin subunit purified from the mollusk *Concholepas concholepas*, known as Loco, and its hemocyanin named CCH.

BACKGROUND OF THE INVENTION

The present invention refers broadly to the use of hemocyanin purified from the mollusk *Concholepas concholepas*, known as Loco, and its hemocyanin named CCH. The structure of this hemocyanin consists of two subunits with common and specific epitopes, which confer an extreme immunogenicity at the level of innate and adaptive immune responses, in all vertebrates in which it has been used. The complex molecular organization of said structure makes it an excellent carrier in the production of antibodies and the formulation of vaccines. It also gives non-specific immuno-stimulant properties when used as an immuno therapeutic agent in the treatment of some types of cancer. Furthermore it is a potent activator for natural killer cells known as NK cells.

Hemocyanins are proteins whose function is the transport of oxygen in a number of mollusk and arthropod species. These proteins contain copper which, when binding oxygen provides the protein its characteristic blue color. Hemocyanins from mollusks and arthropods have a number of applications in immunology, immunochemistry and biotechnology, since they are potent immunogens for inducing the synthesis of a variety of antibodies and also for T specific lymphocytes.

The following are some of these applications:

Use as an experimental antigen in the study of the vertebrate's immune response.

Use as a carrier protein in the production of monoclonal and polyclonal antibodies to different substances, that are not immunogenic (haptens) by themselves, such as synthetic peptides, toxins, medicines, hormones, chemical substances and recombinant microorganisms proteins and plants, animals and human proteins. These antibodies may be used in the production of diagnosis kits, in the detection of organic molecules and in human and animal therapy.

Use as a non-specific immunostimulant in the therapy of some types of cancer.

Use as a diagnosis reagent in some diseases produced by parasites like Schistosomiasis.

In this context, the best-characterized hemocyanin— almost exclusively used for the above mentioned applications—is that known as KLH, hich proceeds from the Keyhole limpet, a Californian mollusk of the species Megathura crenulata.

This expansive use of KLH has led others to seek proteins with similar immune stimulant properties. *Concholepas concholepas* hemocyanin has proven to be a good option in the production of monoclonal and polyclonal antibodies, for instance: against connexin 43, a gap junction protein that regulates the assembly of connexin 33 and connexin 43 in rat Sertoli cell gap junctions (Tan, I. P.; Roy, C., Sáez, J. C.; Sáez, C. G.; Paul, D. I and Risley, M. S. "Regulated assembly of connexin 33 and connexin 43 into rat Sertoli cell gap junctions", Biology of Reproduction vol. 54, pp. 1300–131, 1996); against gizzerosin, a biogenic amine of fish meal (Becker, M. I.; Carrasco I.; Beltran, C.; Torres, M.; Jaureguiberry, B. and De Ioannes, A. E. "Development of monoclonal antibodies to gizzerosine, a toxic component present in fish meal", Hybridoma vol. 17, pp. 373–381, 1998. Torres, M.; Manosalba, H.; Carrasco; De Ioannes, A. E and Becker, M. I. "Specific RIA for gizzerosin and simple procedure labeling method for $^{125}$I-Gizzerosin", Journal of Agricultural and Food Chemistry vol. 47, pp. 4231–4236, 1999); against peptides (Arredondo, M.; Muñoz, P.; Mura, C. and Núñez, M. T. "HFE inhibits apical iron uptake by intestinal epithelial (Caco-2) cells", FASEB Journal vol. 15, pp. 1276–1278, 2001. Mura, C. V.; Becker, M. I.; Orellana, A. and Wolf, D. "Immunopurification of Golgi vesicles by magnetic sorting". Journal of Immunological Methods. vol. 260, pp. 263–71, 2002); and against marine toxin (Córdova, J. L.; Jamett, A.; Aguayo, J.; Faure, M. T., Villarroel, O and Cárdenas, L. "An in vitro assay to detect paralytic shellfish poison", Journal Shellfish Science vol. 29, pp. 55–61, 2001).

Hemocyanin is a glycoprotein found in the hemolymph of some mollusks, which exhibits a high immunogenic capacity in vertebrates, due to its high molecular weight (between $4.5 \times 10^5$ and $9 \times 10^7$, and its phylogenetic origin widely distant from that of vertebrates.

The basic structure of hemocyanin consists in subunits organized as a decamer. In gastropods, decamers are normally associated into di-decamers, which confer them a D5 symmetry that could be considered as similar to a virus. The hemocyanin molecule contains a high number of lysine ε-amino groups, which facilitate their conjugation with other proteins and with haptens. The conjugation is carried out by means of traditional methods based on carbodiimide, glutaraldehyde, or esters of hydroxysuccinimide. One molecule of hemocyanin usually accepts up to 100 hapten molecules without losing its immunogenicity.

W. O. Weigle ("Immunochemical Properties of Hemocyanin", Immunochemistry, vol. 1, pp. 295–302, 1964) describes the immunochemical properties of hemocyanin extracted from Megathura crenulata, however he also demonstrated that the employed preparation comprised at least two antigenic components, according to the diffusion in gel, immuno electrophoresis and electrophoresis in cellulose acetate obtained results.

J. E. Mellema and A. Klug ("Quaternary Structure of Gastropod Haemocyanin", Nature vol. 239, pp. 146 J. E. 150, 1972) demonstrated the existence of a quaternary structure in hemocyanins extracted from three different gastropods (Kellena kelletia, Busycon canaliculatum and Helix pomatia). In all of them, the hemocyanins formed cylindrical particles, and no fundamental differences in their structure have been found.

H. B. Hercowitz, W. W. Harold and A. B. Stavitky ("Immunochemical and Immunogenic Properties of Purified Keyhole Limpet Haemocyanin", Immunology, vol. 22, pp. 51–61, 1972) describe a highly reproducible method to obtain a relatively homogeneous preparation of hemocyanin from Megathura crenulata. In this procedure ionic exchange chromatography in DEAE-cellulose, followed by gel filtration in agarose beads is used. The product obtained was analyzed by agar immunoelectrophoresis, electrophoresis in polyacrylamide gels and by double diffusion in agar. The results show that the purified preparation contained only one main antigenic component, while the raw material contained multiple antigenic components.

J. Markl, A. Savel-Niemann. A. Wegener-Strake, A. Suling, A Schneider, W. Gebauer. J. R. Harris ("The role of two distinct subunit types in the architecture pf keyhole limpet hemocyanin [KLH]", Naturwissenschaften, vol 78, pp. 512–514, 1991) describe the use of transmission electron microscopy with negative staining, ultra centrifugation, dissociation in adequate buffers and subsequent chromatography in polyacrylamide native gels, demonstrating that hemocyanin from Megathura crenulata contains two types of molecules: one formed by 8 functional units, named type-1, and another formed by 7 functional units, named type-2.

J. R. Harris, W. Gebauer and J. Markl ("Immunoelectron microscopy of hemocyanin from the Keyhole Limpet [Megathura crenulata]: A parallel subunit model, Journal of Structural Biology, vol 111, pp. 98–104, 1993) use monoclonal antibodies anti hemocyanin from Megathura crenulata in transmission electron microscopy with negative staining and finding that in each decamer exists an arrangement of subunits in parallel.

R. D. Swerdlow, R. F. Ebert, P. Lee, C. Bonaventura and K. I. Miller ("Keyhole limpet hemocyanin: structural and functional characterization of two different subunits and multimers", Comparative Biochemistry and Physiology, vol. 113-B, pp. 537–548, 1996) demonstrate by immunoelectrophoresis that the two molecular forms described for hemocyanin (KLH-1 and KLH-2) do not exhibit common epitopes and differ in the immune response of experimental animals.

S. M. Söhngen, A. Stahlmann, J. R. Harris, S. A. Müller, A. Engel and J. Markl ("Mass determination, subunit organization and control of oligomerization states of keyhole limpet hemocyanin [KLH]", European Journal of Biochemistry, vol. 248, pp. 603–614, 1997) disclose a study of the structure of KLH-1 and KLH-2 by analytic scan electronic microscopy, electrophoresis in polyacrylamide gels, immunoelectrophoresis, controlled proteolytic digestion and aminoacid sequence.

They demonstrated that these functional subunits differ in both size and the preferential aggregation form. Molecular weights of 400 KDa and 345 KDa were found for KLH-1 and KLH-2, respectively. The KLH-1 subunit has 8 different functional domains; from 45 to 65 Da. Subunit KLH-2 has 7 functional domains and lacks the C-terminal dominion named 1h, present in KLH-1. The subunits differ in their association and dissociation kinetic.

C. A. Olson, R. Chute and C. N. Rao ("Immunologic reduction of bladder cancer recurrence rate", Journal of Urology vol. 111, pp. 173–176, 1974) disclose their observations on specific immunostimulation with Keyhole limpet hemocyanin in 29 patients (26 men and 3 women, between 30 and 93 years of age with a diagnosis of superficial transitional bladder cancer, who had not received X Ray therapy or chemotherapy). Patients were divided into two groups, according to their disease history. Group 1 was formed by 19 patients with 13 episodes of vesical tumor, and received 5 mg hemocyanin subcutaneously at the onset of the study. This group was considered as its own control, since the frequency of the tumors was known through a period of 2 years before treatment. Group 2, consisted of 19 patients with recent diagnosis (1 year) who were treated solely by transuretal resection. On the other hand, 9 patients were immunized with hemocyanin and 10 were not immunized (control group). Through a 2-year follow up, a significant reduction in the tumor recurrence frequency was found in the two groups treated with hemocyanin.

C. D. Jurincic, U. Enggelmann, J. Gasch and K. F. Klippel ("Immunotherapy in bladder cancer and Keyhole limpet hemocyanin. A randomized study" Journal of Urology, vol. 139, pp. 723–726, 1988) describe the results of two studies aimed at evaluating the immunotherapeutic effect of Keyhole limpet hemocyanin on patients with diagnosis of superficial bladder cancer. The first study, initiated in 1982, involved 44 patients who exhibited recurrent superficial bladder cancer. Previously to the therapy, the patients were immunized intracutaneously with 1 mg of hemocyanin, by means of vesical instillation with hemocyanin, and after one month they received 10 mg of hemocyanin by vesical instillation. The control group received monthly 29 mg of Mitomycin C. Twenty-one patients from the hemocyanin treated group (95.2%) exhibited partial and total prevention of the tumor, and 3 patients (14.2%) showed recurrence of the tumor, as compared with 9 patients (38.1%) of the control group. The second study started in 1984 with 81 patients who received the same treatment as in the previous study. In this case there was no control group. It was found that 17 patients (20%) showed recurrence of the tumor and 79 (86.4%) had partial and complete prevention. In the groups treated with Keyhole-limpet hemocyanin, no local or systemic adverse effects were found.

J. Flamm, A Bucher, W. HoltI and W. Albrecht ("Recurrent superficial transitional carcinoma of the bladder: Adjuvant chemotherapy versus immunotherapy. A prospective randomized trial", Journal of Urology, vol. 144, pp. 260–263, 1990) describe the results of a comparative study on the prevention and treatment of the standard therapy of transitional bladder cancer with etoglucids versus immunotherapy with Keyhole limpet hemocyanin, in a universe of 84 patients exhibiting high risk of tumor recurrence. Prior to the onset of the instillations, all patients were submitted to a transuretal removal of the tumor; therefore, they were considered to be free of tumor when starting the treatment. The group of patients treated with etoglucid received 0.565 gm of the same weekly for six weeks and then monthly for one year. The group of patients treated with hemocyanin was immunized with 1 mg of the same intracutaneously and subsequently received vesical instillations of 30 mg during six weeks, then monthly over a year. The recurrence percentage was 60.9% in the group of patients treated with etoglucids versus 55.3% in patients treated with hemocyanin. The difference between both treatments was significant. It was concluded that the immunotherapy of this kind of recurrent tumors with hemocyanin is comparable in efficacy to that of the standard treatment.

D. L Lamm, J. I. Devane, D. R. Riggs and R. F. Ebert ("Immunotherapy of murine bladder cancer with Keyhole limpet hemocyanin (KLH)", Journal of Urology, vol. 149, pp. 648–652, 1993) disclose the results of immunotherapy with Keyhole limpet in an experimental model of bladder cancer in mice C3H/HeN implanted with MBT2 cells, demonstrating that hemocyanin is an immunomodulator with a significant anti-tumoral activity in this animal model.

M. M. Wishahi, I. M. H. Ismail, H. Ruebben and T. Otto ("Keyhole limpet hemocyanin immunotherapy in the bilharzial bladder: A new treatment modality? Phase 2 trial; superficial bladder cancer", Journal of Urology. Vol 153, pp. 926–928) describe the results of the treatment with Keyhole limpet hemocyanin in 13 patients who exhibited transitional bladder tumors associated with urinary schistosomiasis. The authors found that hemocyanin immunotherapy reduced the rate of tumor recurrence to 15.4% as compared with 76.9% before the therapy.

Based on the results of the technique in all the works above mentioned, hemocyanin extracted from the mollusk named Keyhole limpet (Megathura crenulata) has been traditionally used. This hemocyanin is known as KLH (Keyhole Limpet Haemocyanin).

The over exploitation of the Keyhole limpet has resulted in a scarcity of KLH in the international market. The promissory results of immunostimulation and bladder cancer immunotherapy have led to search for other molecules with similar properties. It is important to find alternative substances to replace or supplement KLH, where such new substances must present the adequate characteristics in relation to the immune response. In this context, hemocyanin from Concholepas concholepas is a good option to supplement the use of KLH.

In September 1998, Biosonda S. A. filed a Chilean patent application (Exp.No 2181-98) in the name of Alfredo Emilio De loannes lli, entitled "Purified Hemocyanin from Concholepas concholepas, procedure for its purification, formulation as immunogen and its use as an immunostimulant medicine". Said invention consists in a hemocyanin purified for its use in vertebrates as an immunogenic agent. This hemocyanin is extracted from mollusks other than Megathura crenulata and is obtained in the form of a blue, transparent solution. In the preferred embodiment of the present invention, the mollusk used is Concholepas concholepas (Loco). Moreover a procedure is described for the purification of these hemocyanins consisting in the following operations: a. performing diagonal slits in the foot of the live mollusk, leaving the hemolymph to drain (bleed) for 30 to 60 minutes. b. submitting the hemolymph thus obtained to a saline fractioning and carrying out an ultra filtration, in order to obtain the transparent blue solution, which is rich in hemocyanin. That invention also consists in a formulation comprising hemocyanin, and to the use thereof in the immunization of vertebrates in order to prepare an immunostimulant medicine.

Oliva, H. Moltedo, B., De loannes, P. Faunes F., De loannes, A., and Becker, M. I. ("Monoclonal antibodies in molluskan hemocyanin from Concholepas concholepas demonstrate common and specific epitopes among subunits", Hybridoma and Hybridomics vol. 21. pp. 365–374. 2002) using monoclonal antibodies specific to CCH, characterized by ELISA using different forms of CCH (dissociated in CCH-A and CCH-B subunits, by means of Western blot, enzymatic digestion, chemical deglycosylation and thermal denaturation), demonstrated that the CCH subunit displays common epitopes as well as specific epitopes for CCH-A and CCH-B subunits.

SUMMARY OF THE INVENTION

The present invention refers broadly to the use of hemocyanin purified from the mollusk Concholepas concholepas, known as Loco, and its hemocyanin named CCH. The structure thereof, consisting of two subunits with common and specific epitopes, provides it an extreme immunogenicity—both at the level of innate and adaptive immuno responses—in all vertebrates in which it has been used. The complex molecular organization of said hemocyanin makes it an excellent carrier in the production of antibodies and in vaccines formulation and provides it non specific immuno-stimulant properties when used as an immuno therapeutic agent in the treatment of some types of cancer. It is also a potent activator of NK cells.

Furthermore, it has been found that the new CCH does not require additional divalent cations during the purification process in order to stabilize its structure, being this hemocyanin unique due to its extreme stability. This is a special feature which has not been seen in other molluskan hemocyanins previously described, which require $Ca^{+2}$ or $Mg^{+2}$ for stabilizing their structures (Van Holde, K. E., and Miller, K. I, "Hemocyanins. Advances in Protein Chemistry", vol. 47, pp. 1–81, 1995).

BRIEF DESCRIPTION OF THE DRAWINGS

FIG. 1 shows the SDS-PAGE analysis of CCH under reducing conditions: CCH exhibits the polypeptides CCH-A and CCH-B that were also seen under non-reducing conditions, with an Mr of about 494 kDa and 351 kDa, respectively. Finally, by non-denaturating gel electrophoresis including EDTA in the running buffer, FIG. 1 shows that CCH is dissociated into two polypeptides, indicating that both CCH subunits are held together by non-covalent interactions.

DETAILED DESCRIPTION OF THE INVENTION

Figure 1:
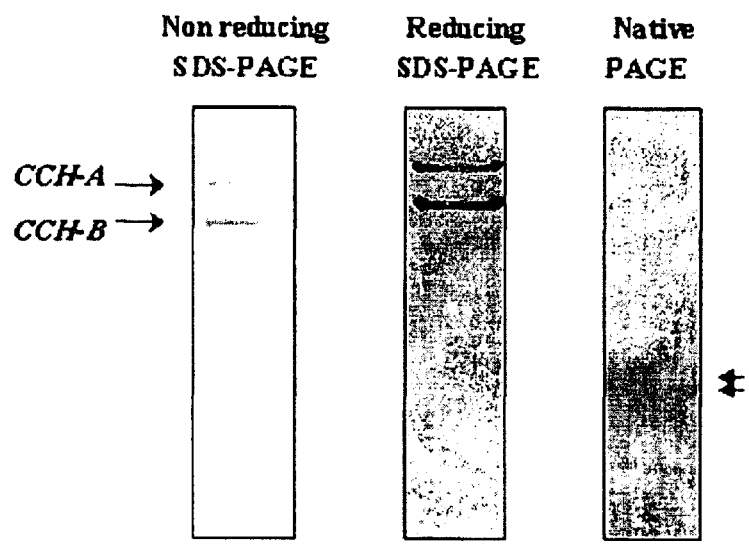
FIG. 1 shows the non-reducing SDS-PAGE electrophoretic pattern of a fresh CCH sample, displaying two non-covalently bound peptides, named CCH-A and CCH-B. Furthermore.

During the studies of CCH-A and CCH-B activity, surprisingly it has been found that the immune response to the isolated CCH-A subunit was significantly higher than that of the isolated CCH-B unit and of the complete molecule. Therefore the main object of the present invention was to develop a new product, method and composition based on the CCH-A subunit.

The present invention is directed to a CCH-A subunit isolated from hemocyanin of the marine gastropod Concholepas concholepas (CCH), for being employed as an immunostimulant in the innate or adaptive vertebrate immune response or as an immunotherapeutic agent for treating cancers in humans or animals, wherein this subunit (CCH-A) has a molecular weight of approximately 404 kDa, is stable in the absence of $Ca^{+2}$ and $Mg^{+2}$, and is at least about 95% pure.

The present invention also involves a method for treating bladder cancer, melanoma, mammary or ovarian cancer, which comprises administering to a patient with bladder cancer an anti-tumor effective amount of a CCH-A subunit, a compound including the purified CCH-A subunit and a physiologically acceptable isotonic buffer.

The concentration of CCH-A subunit in the CCH-A composition is of 0.1–20 mg/ml, preferably 2–10 mg/ml, and most preferably of 5 mg/ml.

The methods for treating bladder cancer, melanoma, mammary or ovary cancer may encompass use of other proteins, lipopolysaccharide (LPS) or other hemocyanins, or their subunits, in combination with CCH-A, or the CCH-A subunit forming heterodimers in different proportions with the *Concholepas concholepas* CCH-B subunit.

In another embodiment, the method for enhancing the immunogenicity of a hapten or peptide includes administration of a composition comprising an immunogen enhancing amount of CCH-A subunit, with said hapten or peptide. In this method, the CCH-A subunit is a carrier for the hapten or peptide, an adjuvant or it is linked to said hapten or peptide.

Moreover, the methods for enhancing the immunogenicity of a hapten or peptide can comprise other proteins, lipopolysaccharides (LPS), other hemocyanins or their subunits, or the CCH-A subunit forming heterodimers, in different proportions with the CCH-B subunit of *Concholepas concholepas*.

The invention also relates to a composition for the treatment of bladder cancer, melanoma, mammary or ovarian cancer, comprising an effective amount of purified CCH-A subunit.

The present invention is described by reference to the following examples, which are offered by way of illustration and they are not intended to limit the invention in any manner. The composition of the hemocyanin is shown on the basis of two subunits presenting common and specific epitopes of each one of them, and how this organization provides a high degree of immunogenicity, either as a complete molecule or by way of one of its subunits, the one named CCH-A. The usefulness of hemocyanin as immunotherapeutic agent is also shown in the treatment of superficial bladder carcinoma in mice as well as its potentiating effect on the NK cells activity. Standard techniques well known in the art or the techniques specifically described below were used.

EXAMPLE 1

Composition of CCH on the Basis of Two Subunits Named CCH-A and CCH-B

Procedure

SDS-PAGE-Electrophoresis. The technique was performed as described by Laemmli (Laemmli U. K., "Cleavage of structural proteins during the assembly of the head of the head of bacteriophage T4", Nature vol. 227, pp 680–685, 1970) in a gradient version, with a separating gel from 3% to 12% polyacrylamide and a 3% stacking gel. Protein samples were heated for 5 min at 100° C. in the presence of SDS and DIT or β-Mercaptoethanol. Gels were run at 70 V during 12 h at room temperature. Molecular weights were estimated from band mobility with a calibration curve obtained from KLH-2 bands and pre-stained markers. The gels were then fixed and stained with Coomassie blue.

Native gel electrophoresis: The procedure described by Swerdlow et al., was applied (Swerdlow, R. D., Ebert, R. F., Bonaventura C., and Miller K. I. "Keyhole limpet hemocyanin: Structural and functional characteristics of two different subunits and multimers". Comp. Biochem. Physiol. B Biochem Mol., vol. 113, pp. 537–548, 1996). This system requires dissociating conditions on a polyacrylamide gradient gel, with a buffer containing 140 mM Tris, 90 mM boric acid and 2.5 mM EDTA at pH 8.6. Prior to electrophoresis, samples were dissociated by incubation in the sample buffer at 4° C. Separations were performed at room temperature during 24 h at 80 V. Finally, gels were fixed and stained with Coomassie blue.

Amino acid composition: The amino acid analysis was performed at the Protein/DNA Technology Center, Rockefeller University, USA. Samples were hydrolyzed for 22 h at 110° C. in 6N HCl containing 1% Phenol. Waters PICO TAG equipment was employed, using Waters' Millenium software, 510 Pump, and 490 detectors. A Waters' Novapak C18, 30-centimeter column was used. Mol percent values were obtained from 9.18 μg and 12.53 μg of hydrolyzed protein from isolated subunit CCH-A and CCH-B, respectively.

Amino acid sequence: Soluble samples of CCH Mono-Q isolated subunits, and fresh and aged CCH that were subjected to SDS-PAGE and transferred to PVDF membranes were sequenced by Edman degradation at the Protein/DNA Technology Center, Rockefeller University, USA. For the sequence analysis Clustal X program was used.

Results

Polypeptide Chains of CCH. FIG. 1 shows the non-reducing SDS-PAGE electrophoretic pattern of a fresh CCH sample, displaying two non-covalently bound peptides, named CCH-A and CCH-B. Also, FIG. 1 shows the analysis of CCH by SDS-PAGE under reducing conditions: CCH exhibits the polypeptides CCH-A and CCH-B that were also seen under non-reducing conditions, with an Mr about 494 kDa and 351 kDa, respectively. Finally, FIG. 1 shows non-denaturating gel electrophoresis including EDTA in the running buffer; CCH is dissociated into two polypeptides, indicating that both CCH subunits are held together by non-covalent interactions.

The N-terminal sequence analysis on CCH-A subunits isolated by Mono-Q column was performed up to residue 10, and it was LMRKDVDTLT; and for CCH-B subunit up to residue 7, it was LXRKNVD, The N-terminal region of hemocyanins have a conserved motif which is underlined. In Table 1 the Amino acid composition of CCH-A and CCH-B is presented.

TABLE 1

Aminoacid composition in Mole % of CCH-A and CCH-B subunits

| Amino Acid | CCH-A | CCH-B |
|---|---|---|
| Ala | 7.8 | 8.1 |
| Arg | 5.0 | 5.9 |
| Asn | 7.3 | 5.7 |
| (Cys)[2] | ND* | ND |
| Glu | 11.1 | 10.2 |
| Gly | 3.1 | 3.3 |
| Hys | 4.5 | 4.6 |
| Ile | 4.5 | 4.7 |
| Leu | 13.2 | 14 |
| Lys | 1.0 | 1.5 |
| Met | 2.6 | 2.3 |
| Phe | 11.1 | 10.5 |
| Pro | 9.9 | 9.4 |
| Ser | 1.6 | 1.5 |
| Thr | 4.3 | 4.7 |
| Trp | ND | ND |
| Tyr | 5.9 | 5.9 |
| Val | 6.9 | 7.7 |

*Not Determined

EXAMPLE 2

Isolation Procedure and Characterization of *Concholepas concholepas* CCH-A Subunit Procedure Isolation of CCH-A subunits. The general procedure described by Swerdlow, et al., was employed (Swerdlow, R. D.; Ebert, R. F., Bonaventura, C. and Miller K. I. "Keyhole limpet hemocyanin: structural and functional characterization of two different subunits and multimers", Comp. Biochem. Physiol B Biochem Mol. Biol. vol. 113 pp. 537–548, 1996) with minor modifications. Highly purified and LPS free CCH in PBS, without $Ca^{+2}$ and $Mg^{+2}$, were dissociated by dialysis against 5 volumes of 130 mM Glycine-NaOH pH 9.6, 10 Mm EDTA overnight at 4° C. Dissociated CCH was applied on a Mono-Q 5/5 column at a flow rate of 1.0 ml/min. To elute the column, a solution of 130 mM Glycine-NaOH pH 9.6 10 mM EDTA (solvent A) and A solvent plus 1 M NaCl (solvent B) were used. The elution program was as follows: once the sample is applied, the column is equilibrated with solvent A during 5 min, then a linear gradient from 0 to 70% of solvent B (30 min) is applied, followed by a 5 min washing with 70% solvent B. Mono-Q chromatography was monitored at 280 nm.

Dialysis of subunit CCH-A. The isolated CCH-A subunit was dialyzed against PBS (phosphate buffer saline, 0.1 M sodium phosphate, 0.15 M NaCl, pH 7.2) without adding divalent ions. The concentration and the quality of the preparation were determined by SDS-PAGE. As control, the same procedure was carried out with subunit CCH-B. To determine the quality of subunit CCH-A, aggregation assays were carried out with the isolated subunit CCH-B, and were monitored by light scattering and transmission electron microscopy.

Light Scatterinq studies: The experiments were carried out according to van Holde, et al., (Van Holde, K. E., Miller, K., Schabtach, E. and Libertini, L. "Assembly of Octopus dofleini hemocyanin. A study of the kinetic by sedimentation, light scattering and electron microscopy", J. Mol. Biol. vol 217 pp. 307–321, 1991) with minor modifications. CCH subunits purified by Mono-Q chromatography were used in a Perkins Elmer Spectrofluorometer. Scattered light was measured at 90° to the incident beam with both entrance and exit monochromators set to 384 nm. The re-association experiments were carried out at 20° C. and Tris.HCl 100 mM pH 7.6 $MgCl_2$ 50 mM. $CaCl_2$ 10 mM buffer was added. Samples of electron microscopy analysis were taken, and then the procedure was continued as described in example 3.

Results

Figure 2A:
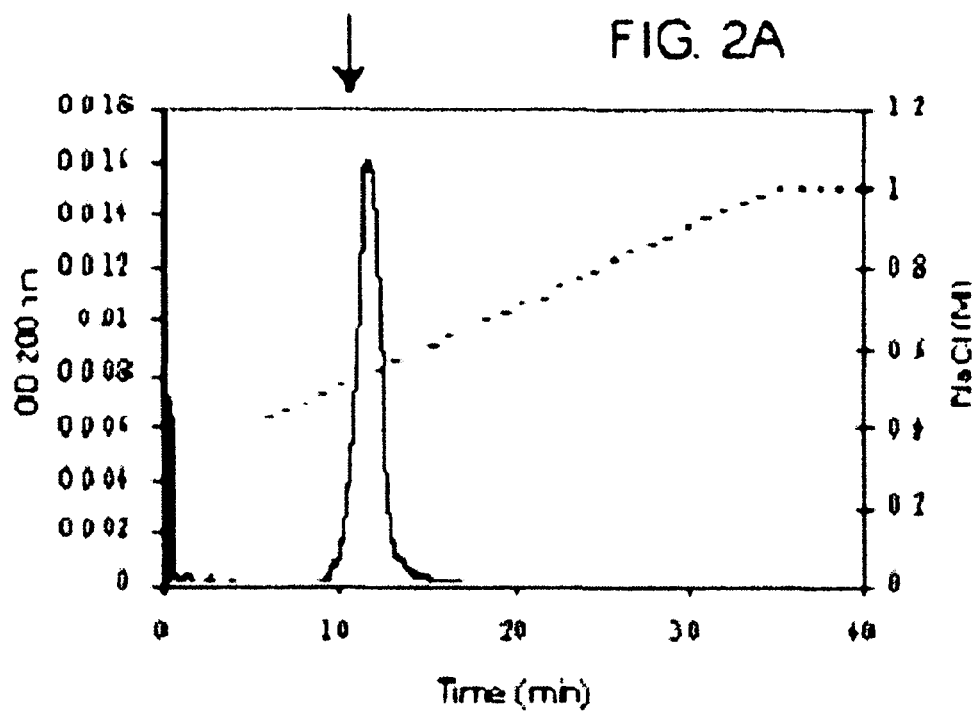
FIG. 2A shows anion-exchange chromatography of whole CCH on a Mono-Q FPLC column with a linear NaCl gradient for sample elution, obtaining one symmetric peak
Figure 2B:
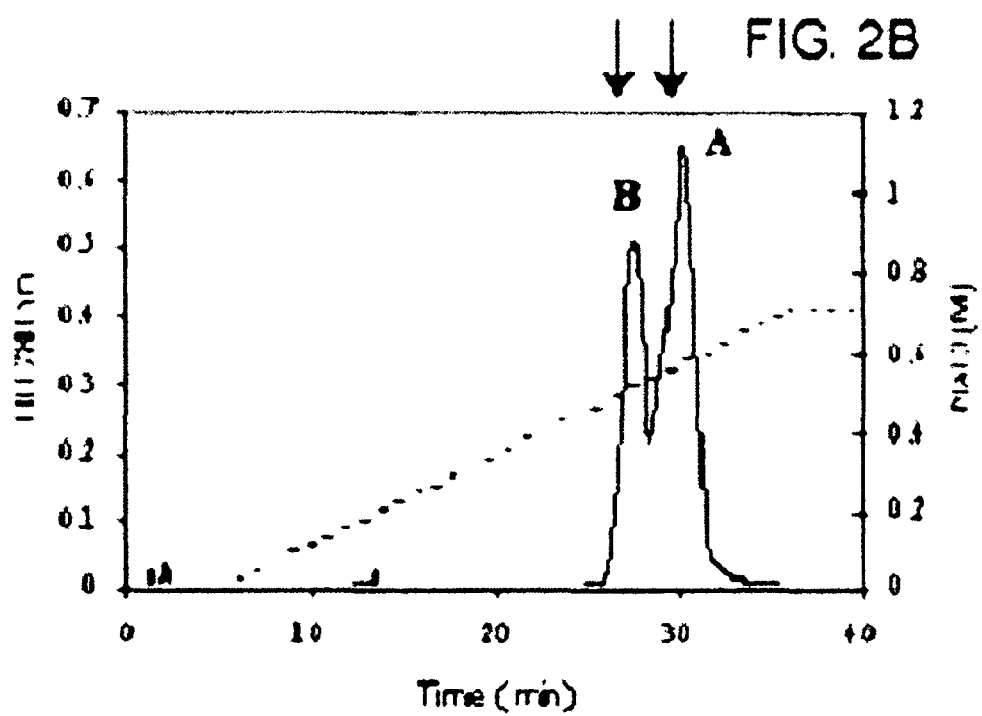
FIG. 2B shows anion-exchange chromatography of dissociated CCH on a Mono-Q FPLC column with a linear NaCl gradient for sample elution, obtaining two peaks.
Figure 2C:
FIG. 2C is an electron microscopy image of both peaks obtained from dissociated CCH shown in FIG. 2B, after negative staining, showing only globular disorganized structures.
Figure 2D:
FIG. 2D is an electron microscopy image of the peak obtained from control CCH shown in FIG. 2A, after negative staining.
Figure 2E:
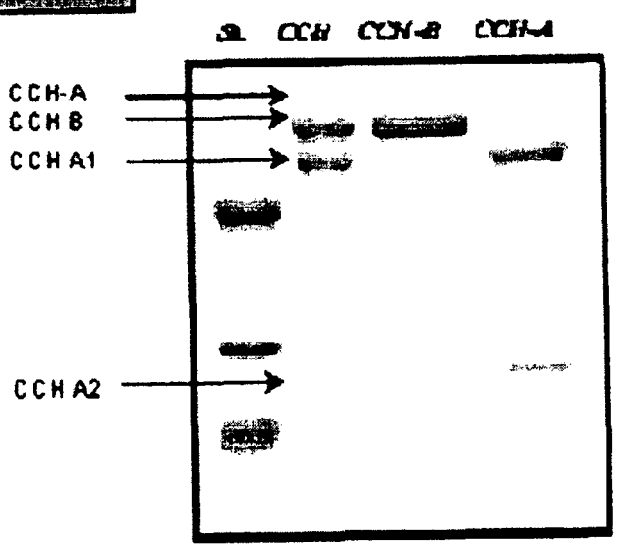
FIG. 2E shows An SDS-PAGE analysis of the fractions of both peaks, indicating that peak A contained CCH-A1 and CCH-A2, whereas peak B contained CCH-B.

To analyze the subunit composition of CCH, we subjected the protein to anion-exchange chromatography on a Mono-Q FPLC column with a linear NaCl gradient for sample elution. When whole CCH was applied to the column, we obtained one symmetric peak (FIG. 2A). In contrast, two peaks were observed for dissociated CCH (FIG. 2B). Both peaks obtained from dissociated CCH were analyzed by electron microscopy after negative staining; only globular disorganized structures were present (FIG. 2D) as compared to CCH control (FIG. 2C). SDS-PAGE analysis of the fractions indicated that peak A contained CCH-A1 and CCH-A2 whereas peak B contained CCH-B (FIG. 2E).

Figure 3:
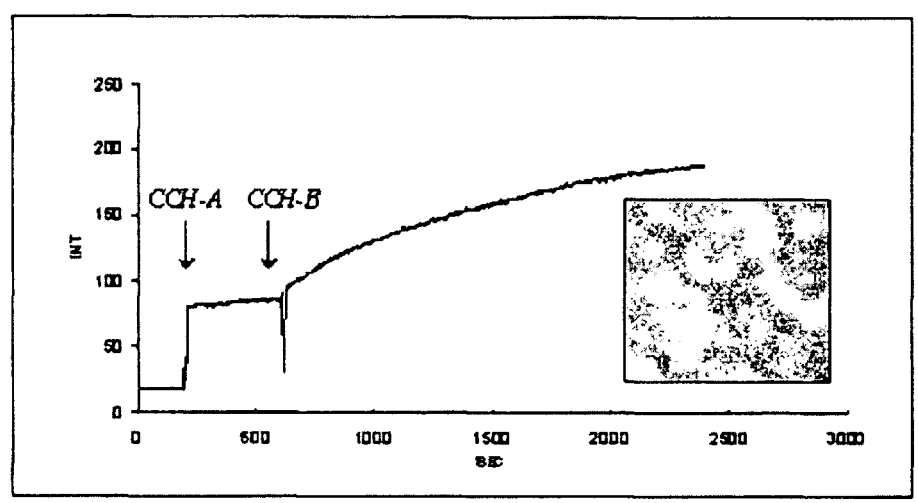
FIG. 3 shows the association phenomenon measurable by increment in light scattering of the material formed during the association of CCH-A to CCH-B, as observed by negative staining on the transmission electron microscope.

The integrity of the isolated CCH-A subunit was determined by means of aggregation assays with the CCH-B subunit, isolated in the same way, using light scattering. In prior experiments, carried out with the complete molecule, it was observed that, when it was found in dissociating conditions it did not exhibit the association phenomenon measurable by increment in light scattering. However, when subunit CCH-A was placed under association conditions, in the presence of subunit CCH-B, an increase in fluorescence was observed in time. The material formed during the association of CCH-A to CCH-B, observed by negative staining on the transmission electron microscope, is shown in the box of FIG. 3 and corresponds to the normal structure of the C. concholepas hemocyanin.

EXAMPLE 3

The hemocyanin from Concholepas concholepas does not require additional $Ca^{+2}$ or $Mg^{+2}$ to keep its structures intact.

Procedure

Hemocyanin purification. The general procedure described by Herskovits, T. T. Hamilton, M. G. Mazzella, L. J ("Haemocyanin of the chiton Acanthopleura granulata". Biochemistry, vol. 25, pp. 3612–3619, 1986) with modifications, was employed. Live Concholepas concholepas specimens were transported to the laboratory in seawater. The hemolymph, collected by bleeding at 4° C., through several diagonal slits made on mantel and foot of the mollusk, was filtered through a glass fiber mesh. The hemocytes and other cells were removed by centrifugation at 1,400 g during 20 min, at 4° C., and sodium azide was added to a final concentration of 0.1%. The material was precipitated for 12 h at 4° C. with 33% (w/v) crystalline ammonium sulfate, and centrifuged at 4° C. for 1 h at 16.300 g in a Sorvall centrifuge. The colorless crystalline supernatant was discarded. Precipitation and concentration procedures were done twice. The CCH pellet was then suspended in PBS (phosphate buffer saline, 0.1 M sodium phosphate, 0.15 M NaCl, pH 7.2). This material was dialyzed at 4° C. against PBS to remove ammonium sulfate. CCH was pre-filtered using a 0.22 μm in a Seitz filter unit and sterilized through a 0.22 μm filter unit, then stored at 4° C. Protein concentration was determined using Coomassie blue or Bicinchoninic acid protein kits according to the manufacturer's instructions. This hemocyanin preparation was considered highly pure by gel chromatography and dodecylsulfate-polyacrylamide gel electrophoresis (SDS-PAGE).

Electron Microscopy. The general procedure described by Fernández-Morán, H., Van Bruggen E. F. J. and Ohtsuki, M. (Macromolecular organization of hemocyanins and apo-hemocyanins as revealed by Electron Microscopy. J. Molecular Biology, 16, pp. 191–207, 1966) was used with minor modifications. Twenty-microliter aliquots of CCH samples (0.5 to 1 mg/ml) were applied during 1 min to Formvar or Parlodion coated copper grids, previously stabilized by vacuum evaporation on a carbon coat. They were stained for periods from 1 to 3 min with 20 μl of 1% to 2% aqueous uranyl acetate solution previously filtered through a 0.22 μm filter. The grids were air-dried at room temperature and observed under a Tecnai 12 electron microscope.

Results

During purification of CCH and after being stored for an extended time, we have never used additional divalent cations in the buffers, at difference with almost all molluskan hemocyanins previously described that require $Ca^{+2}$ or $Mg^{+2}$ to stabilize its enormous structures. CCH samples stored in PBS at 4° C. during for at least 4 years, kept intact their quaternary structure intact. (See FIG. 4).

Figure 4:
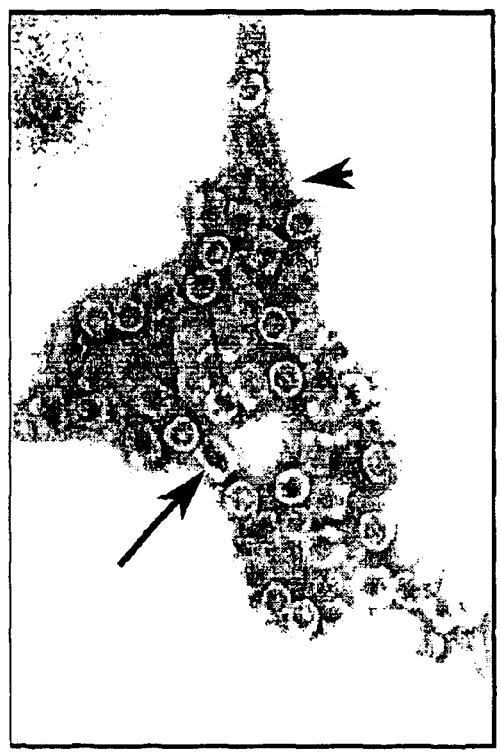
FIG. 4 shows an electron microscope preparation of purified CCH molecules negatively stained with uranyl acetate. Circular specimens of about 325 Å in diameter and rectangular specimens of about 792 Å in height were observed.

FIG. 4 shows an electron microscope preparation of purified CCH molecules negatively stained with uranyl acetate. Circles of about 325 Å in diameter and rectangular specimens of about 792 Å in height were observed. The figure illustrates molecules displaying typical subunit structures, arranged in layers of 6 parallel rows. Didecamers (see arrow →) were the most frequent forms observed, while decameric (see arrow head ▶) or multi-decameric structures were scarce

EXAMPLE 4

Immunization with Isolated Subunits of *Concholepas concholepas* Hemocyanin a. Procedure In order to compare the immunogenicity of each one of the subunits isolated from the hemocyanin obtained from *Concholepas concholepas*, two mice per group of the C57B1 strain were immunized in parallel with CCH-A, CCH-B, and with the complete molecule as control. The immunization protocol of the mice is described below in Table 2. Prior to the treatment, blood samples were taken from each mouse to have a sample of pre-immune serum as control.

TABLE 2

| Day | Protocol |
|---|---|
| Day 1 | 400 μg of antigen in Incomplete Freund's Adjuvant, subcutaneous and intradermic |
| Day 20 | 400 μg of antigen in Incomplete Freund's Adjuvant, subcutaneous and intradermic |
| Day 40 | Bleeding of secondary immune response to determine the humoral immune response in serum by ELISA |

The presence of specific antibodies to the antigen used for immunization was determined by an immuno enzymatic assay in solid phase (ELISA), on a 96 micro well polystyrene plate covered with 10 μg ml of the antigen. To determine the presence of specific antibodies in the serum of immunized mice, an alkaline phosphatase-conjugated mice anti Goat IgG was used. The assay was revealed with the chromogenic substrate para-nitro-phenyl-phosphate (pNPP). Plates were read spectrophotometrically at 405 nm.

b. Results

The results are presented in FIG. 5 and data were plotted as follows: each antigen in evaluation was placed on the abscissa and the titer of seric antibodies of each group was placed on the ordinate. The titer was defined as the dilution of the serum wherein half of the optical density is read.

Figure 5:
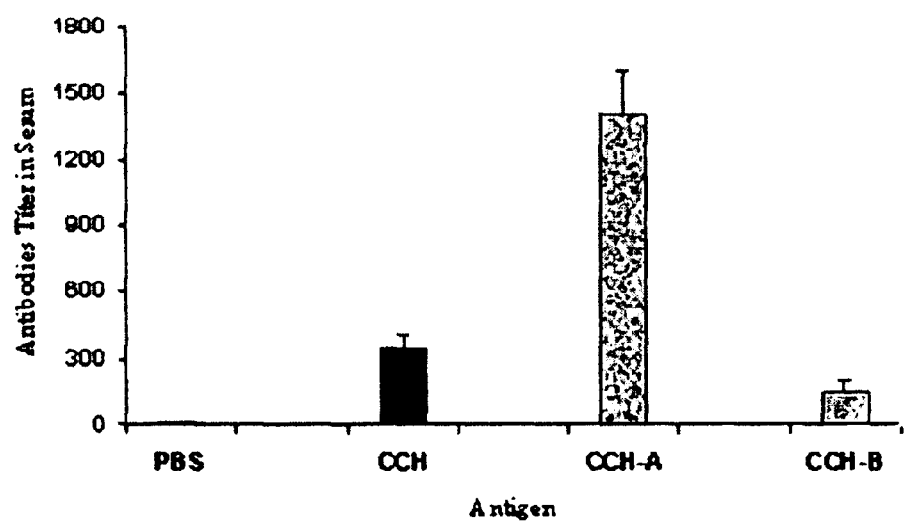
FIG. 5 shows that the immune response to the isolated CCH-A subunit is significantly higher than those of the isolated CCH-B unit and of the complete CCH molecule.

FIG. 5 shows that the immune response to the isolated CCH-A subunit is significantly higher than that of the isolated CCH-B unit and of the complete molecule The exposition done in the present descriptive memory has to be interpreted in ample terms. The examples should be interpreted only as illustrations, and not as limiting terms.

We claim:

1. A composition comprising:
   a. a product consisting essentially of a disassociated CCH-A subunit isolated from hemocyanin of the marine gastropod *Concholepas concholepas*, wherein the CCH-A subunit has a molecular weight of about 404 kDa, is stable in the absence of $Ca^{+2}$ and $Mg^{+2}$, and
   b. a physiologically acceptable isotonic buffer.

2. The composition according to claim 1, wherein the composition further comprises another protein, an LPS, a polysaccharide, or another hemocyanin or a subunit thereof, wherein the CCH-A subunit it at least 95% pure.

3. The composition according to claim 2, wherein the other hemocyanin comprises a dissociated CCH-B subunit.

4. A method for treating a disease state selected from bladder cancer, melanoma, mammary cancer or ovary cancer, comprising the step of administering to a patient with the disease state an effective anti-tumor amount of a composition comprising:
   a. a product comprising a dissociated CCH-A subunit isolated from the hemocyanin of the marine gastropod *Concholepas concholepas*, wherein the CCH-A subunit has a molecular weight of about 404 kDa, is stable in the absence of $Ca^{2+}$ and $Mg^{2+}$ and is at least 95% pure, and
   b. a physiologically acceptable isotonic buffer.

5. A method according to claim 4 wherein the composition further comprises another protein, a LPS, a polysaccharide or another hemocyanin or a subunit thereof.

6. The method of claim 5 wherein the other hemocyanin is a dissociated CCH-B subunit.

7. The method according to claim 4, wherein the composition comprises a concentration of CCH-A subunit from about 0.1 mg/ml to 20 mg/ml.

8. The method according to claim 7, wherein the concentration of CCH-A subunit is from about 2 to 10 mg/ml.

9. The method according to claim 8, wherein the concentration of CCH-A subunit is 5 mg/ml.

10. A method for enhancing the immunogenicity of a hapten or a peptide, comprising the step of administering with the hapten or the peptide an amount of a product comprising a dissociated CCH-A subunit isolated from the hemocyanin of the marine gastropod *Concholepas concholepas*, wherein the CCH-A subunit has a molecular weight of about 404 kDa, is stable in the absence of $Ca^{2+}$ and $Mg^{2+}$, is at least 95% pure, and wherein the product is an immunogen.

11. The method according to claim 10, wherein the CCH-A subunit is a carrier for the hapten or peptide.

12. The method according to claim 10, wherein the CCH-A subunit is an adjuvant.

13. The method according to claim 10, wherein the CCH-A subunit is linked to the hapten or peptide.

14. The method according to claim 10, wherein the product further comprises a dissociated CCH-B subunit.

15. A method for immunostimulating the innate or adaptive response of vertebrates comprising administering a therapeutically effective amount of a dissociated CCH-A subunit from *Concholepas conchcolepas* as an immunotherapeutic agent to treat cancers or tumors found in animals or humans.

* * * * *